(12) United States Patent
Brooks

(10) Patent No.: US 7,854,711 B2
(45) Date of Patent: Dec. 21, 2010

(54) ARM SLING AND METHOD OF MAKING

(76) Inventor: Lucille S. Brooks, 3153 Washburn, Vassar, MI (US) 48768

( * ) Notice: Subject to any disclaimer, the term of this patent is extended or adjusted under 35 U.S.C. 154(b) by 526 days.

(21) Appl. No.: 11/368,219

(22) Filed: Mar. 6, 2006

(65) Prior Publication Data

US 2007/0208286 A1    Sep. 6, 2007

(51) Int. Cl.
*A61F 5/00* (2006.01)
(52) U.S. Cl. .................. 602/4; D29/120.1; D24/190; D24/193
(58) Field of Classification Search .............. 602/4, 602/20, 21, 36; 5/89.1; D29/120.1; D24/190, D24/193
See application file for complete search history.

(56) References Cited

U.S. PATENT DOCUMENTS

| | | | |
|---|---|---|---|
| 1,266,688 A | 5/1918 | Kassner | |
| 1,621,323 A | 8/1926 | Horn | |
| 2,088,927 A | 8/1937 | Roy | |
| D222,898 S | 1/1972 | Morris | |
| D235,928 S | 7/1975 | Moore | |
| 4,572,172 A | 2/1986 | Williams | |
| 5,358,470 A | 10/1994 | Johnson | |
| 6,099,489 A | 8/2000 | Herzberg et al. | |
| 6,110,133 A | 8/2000 | Ritts | |
| 6,592,539 B1 | 7/2003 | Einarsson et al. | |
| 6,595,936 B1 | 7/2003 | Oladipo | |
| 6,730,052 B2 | 5/2004 | Chow | |
| 6,923,778 B1 | 8/2005 | Cheng | |
| 2006/0189906 A1* | 8/2006 | Nelin et al. | 602/4 |
| 2006/0258966 A1* | 11/2006 | Hargrave et al. | 602/20 |

* cited by examiner

*Primary Examiner*—Patricia M Bianco
*Assistant Examiner*—Tarla R Patel
(74) *Attorney, Agent, or Firm*—Robert L. McKellar; McKellar IP Law, PLLC

(57) ABSTRACT

An arm sling and method of making an arm sling including an open ended arm receiving tube supported on a patient's neck via a neck strap. The tube includes a forward end portion with an open front end of predetermined size and a rear end portion having an elbow receiving pocket adjacent an enlarged diameter rear opening. The arm receiving tube is formed from a single sheet of pliable fabric and includes first and second elongate opposing substantially identical side wall panels each having upper and lower edges spanning front and rear edges which form the front and rear openings. Each lower edge includes a front lower edge portion longer than the upper edge and a rear lower edge portion which is shorter than the upper edge. The rear lower edge portion is upwardly inclined relative to the front lower edge and has a rear end terminating in the lower end of the rear edge.

38 Claims, 4 Drawing Sheets

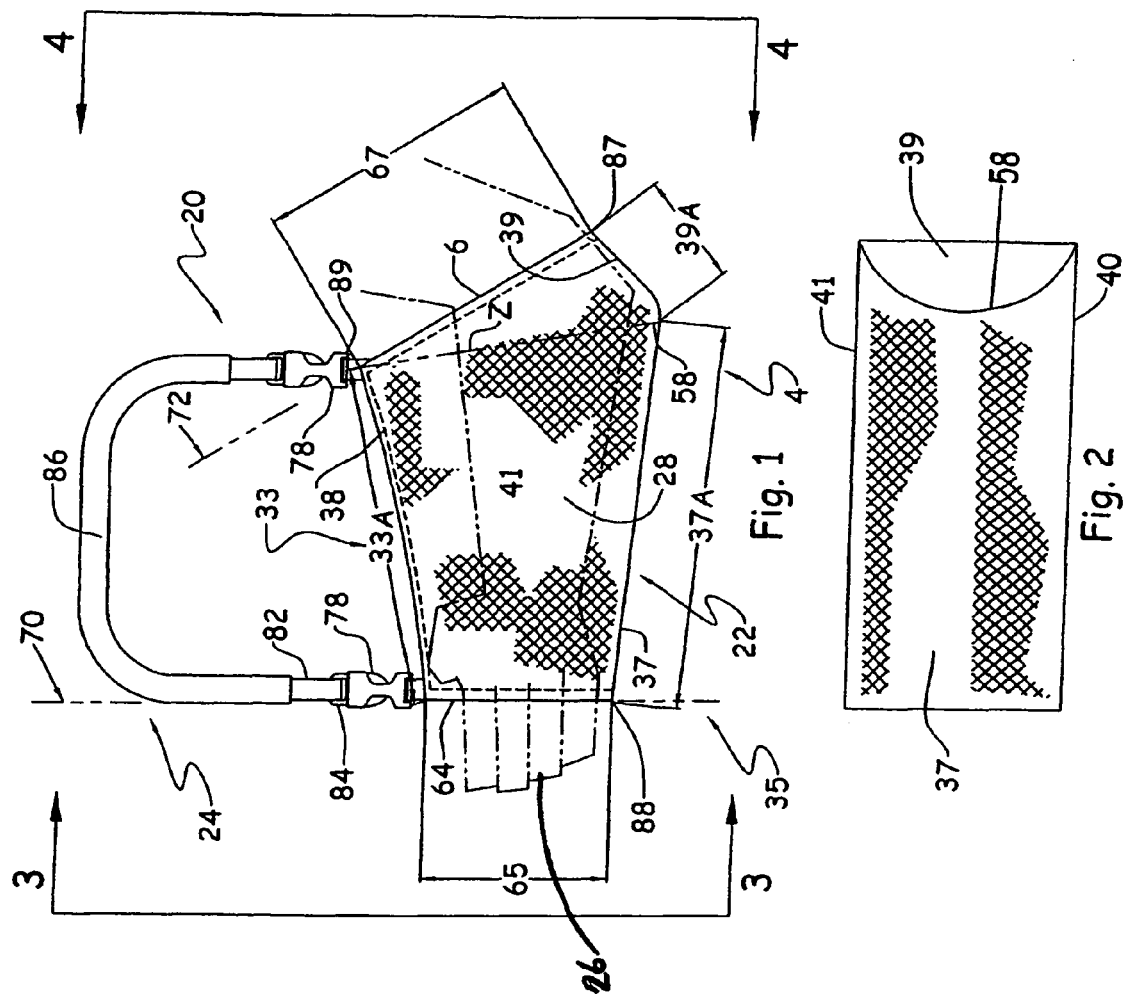

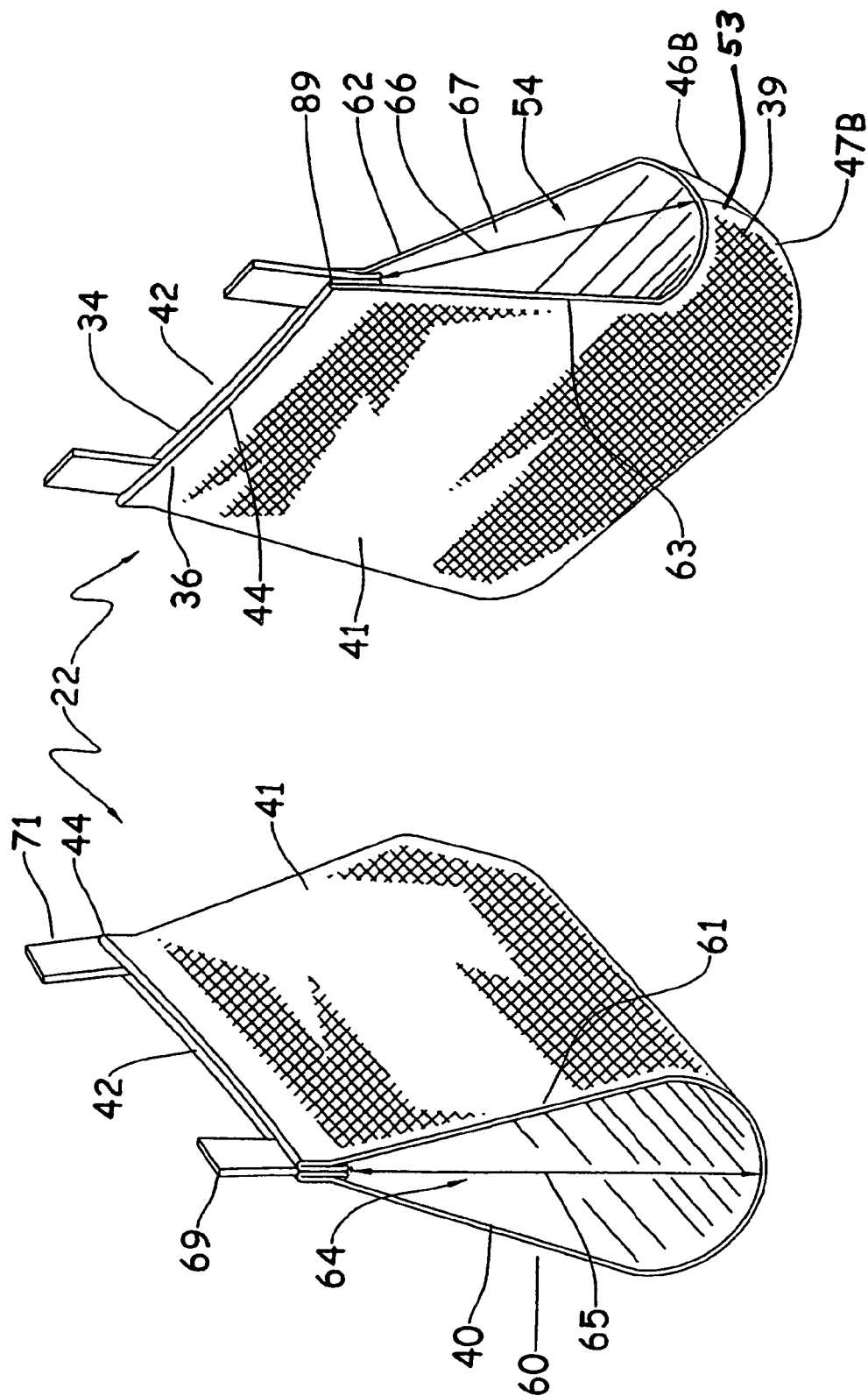

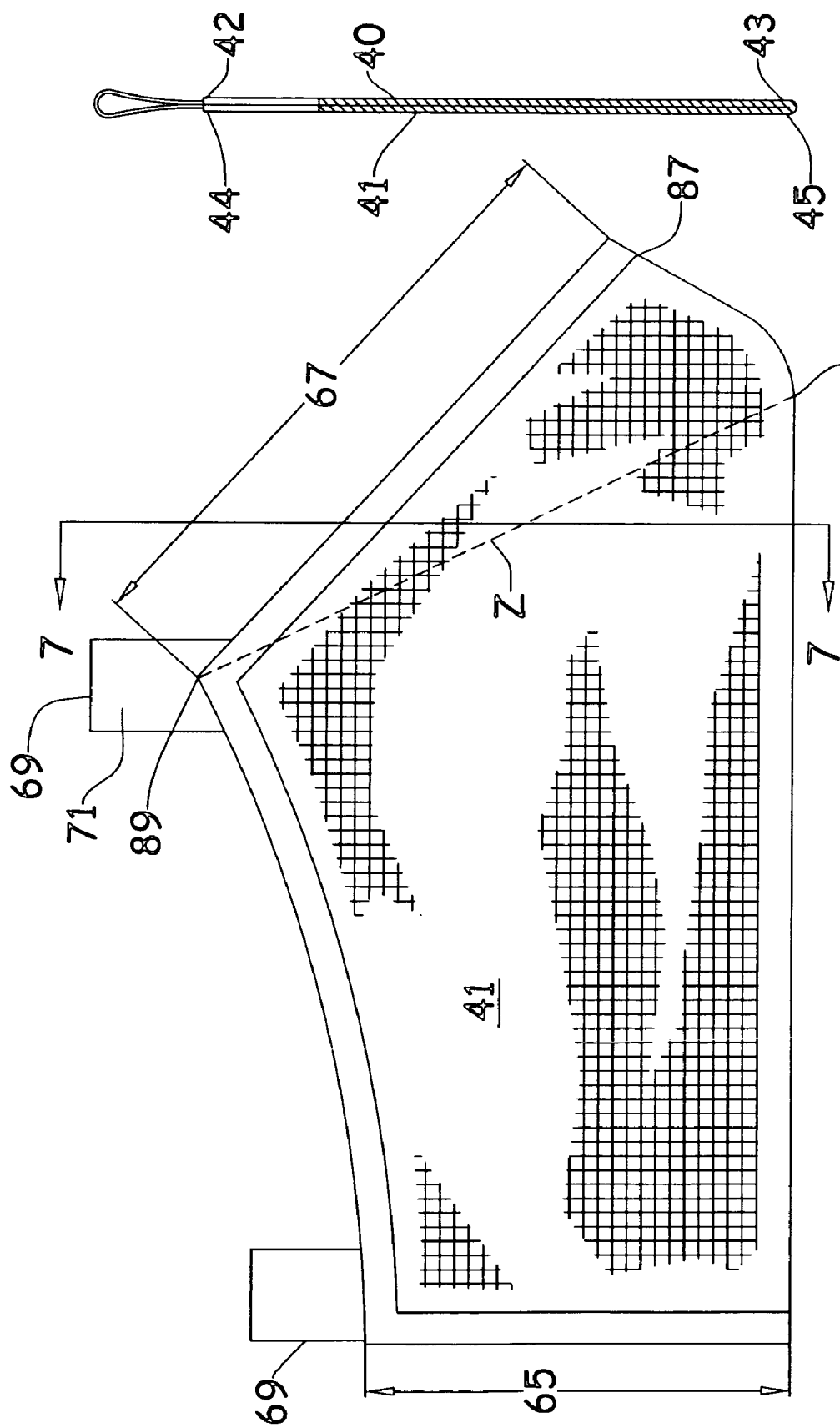

ated in FIGS. 1-4; and

ARM SLING AND METHOD OF MAKING

BACKGROUND OF THE INVENTION

1. Field of the Invention

This invention relates to an arm sling and more particularly to a new and improved tubular arm sling.

2. Description of Prior Art and Objects

Arm slings have been provided heretofore such as that illustrated in U.S. Pat. No. 2,088,927 issued to D. Roy on Aug. 3, 1937, U.S. Pat. No. 4,572,172 issued to L. Benton Williams on Feb. 25, 1986 and U.S. Pat. No. 6,110,133 issued to Graham Douglas Ritts on Aug. 29, 2000. These slings are sometimes referred to as "open top-closed elbow" slings which can be difficult to install and somewhat dangerous as a patient's arm inadvertently can fall out of the prior art sling.

Other prior art slings such as those illustrated in U.S. Pat. No. 1,266,688 issued to J. C. Kassner on May 21, 1918, U.S. Pat. No. 5,358,470 issued to James Johnson on Oct. 25, 1994, U.S. Pat. No. 1,621,323 issued to E. M. Horn on Aug. 21, 1926; U.S. Pat. No. 6,595,936 B1 issued to Olarewaju J. Oladipo on Jul. 22, 2003; and U.S. Design Pat. No. 235,928 include fold over members that do not secure the elbow and allow the arm to inadvertently slip out of the sling.

The following additional U.S. Patents are cited to demonstrate other various medical appliances:

| U.S. Pat. No.: | Patentee | Issued |
| --- | --- | --- |
| Des. 222,898 | Eleanor Morris | Jan. 25, 1972 |
| 6,099,489 | Herzberg, et al | Aug. 8, 2000 |
| 6,592,539B1 | Einarsson, et al | Jul. 15, 2003 |
| 6,730,052B2 | James C. Y. Chow | May 4, 2004 |
| 6,923,778B1 | Pay-Zen Cheng | Aug. 2, 2005 |

The present invention contemplates a new and novel tubular arm sling which includes an open ended arm support sleeve of pliable material having a front end which gradually rearwardly increases in breadth from a front opening of predetermined breadth to a rear end portion having a rear end opening of a greater predetermined breadth, an intermediate elbow receiving tubular portion between the front and rear ends of a still greater breadth, and a sleeve supporting neck strap.

The open ended tube includes opposing substantially identical pliable fabric side wall panels each having upper and lower borders spanned by front and rear edges which define the front and rear openings. Each of the lower borders includes a front lower border portion which is longer than the upper border and rearwardly diverges away from the upper border and a rearward lower border portion, which is upwardly rearwardly inclined relative to, and is substantially short than, the front lower forward border portion. The tube includes an elbow receiving pocket for receiving the elbow and inhibiting the inadvertent removal of the elbow.

One aspect of the invention includes the method of making the arm sling support tube with a one-piece sheet of pliable fabric which is folded over on itself and coupling the terminal ends together to form the front portion of the sleeve and also securing the lower rear edge portions together to form an elbow receiving pocket.

These and other advantages of the present invention will become more readily apparent of those of ordinary skill and the art as the description thereof proceeds:

SUMMARY OF THE INVENTION

An arm sling comprising an open ended arm support tube including a closed sidewall defining an elongate passage having a forward end opening of a predetermined breadth and diverging rearwardly to an elbow receiving pocket of a second greater predetermined breadth and thence rearwardly converging to a rear terminal end opening of a third predetermined breadth which is greater than the first predetermined breadth and less than the second predetermined breadth, and a neck strap for dependently supporting the tube.

DESCRIPTION OF THE DRAWINGS

The invention may be more readily understood by reference to the accompanying drawings, in which:

FIG. 1 is a side elevational view of a new and novel arm sling constructed according to the present invention;

FIG. 2 is a bottom view thereof;

FIG. 3 is an end perspective view of the tubular arm support only taken along the line 3-3 of FIG. 1;

FIG. 4 is an opposite end perspective view of the tubular arm support only taken along the line 4-4 of FIG. 1;

FIG. 6 is a side elevational view illustrating the arm support tube in a subsequent step in the assembly of the sling illustrated in FIGS. 1-4; and FIG. 7 is a sectional end view taken along the section line 7-7 of FIG. 6

DESCRIPTION OF PREFERRED EMBODIMENT

Figure 5:
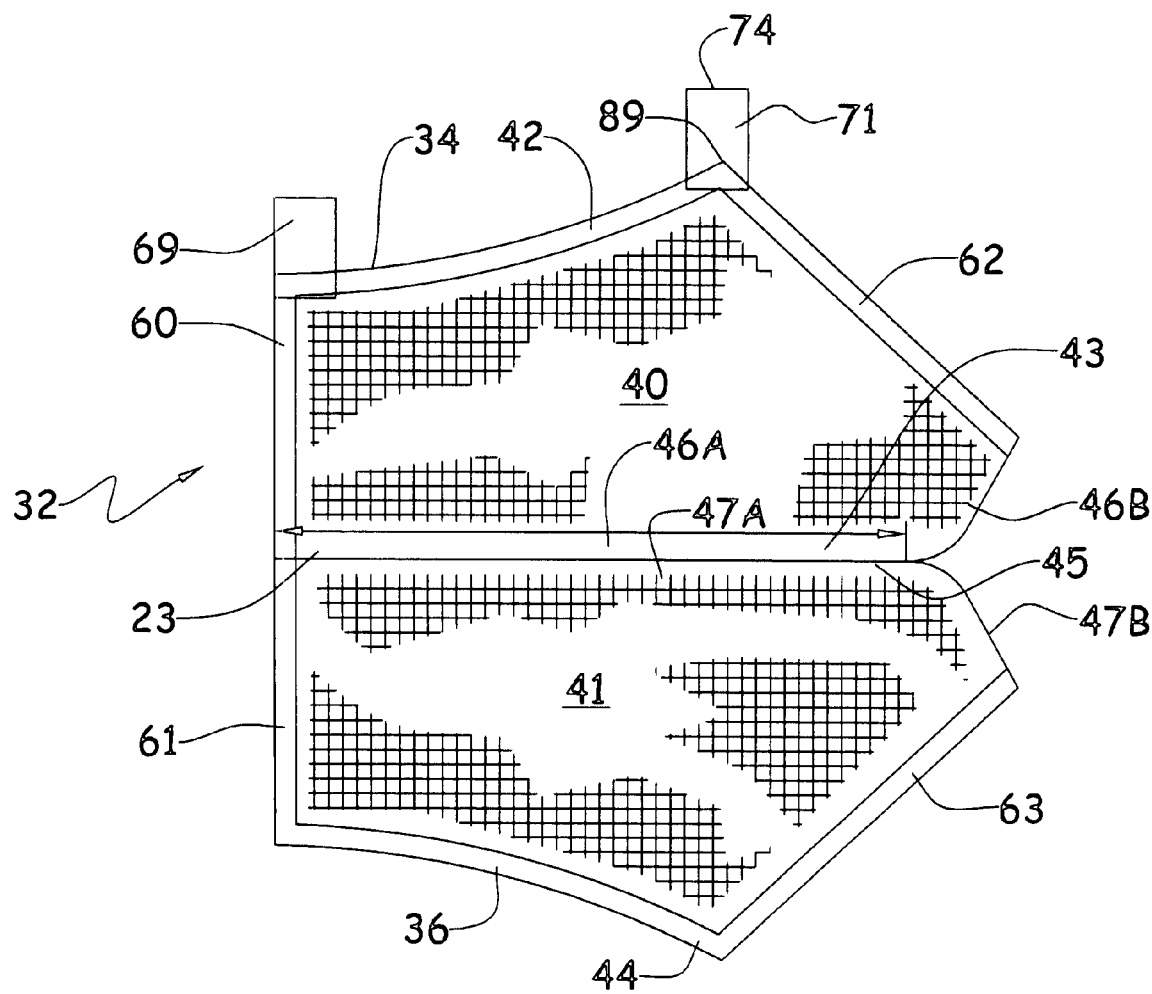
FIG. 5 is a plan view, a slightly enlarged pattern sheet utilized in making the tubular portion of the sling illustrated in FIGS. 1-4.

An arm sling, generally designated 20, includes a tubular arm support 22 and a neck strap 24, for detachably receiving a patient's arm, generally illustrated in chain lines at 26. The tubular arm support 22 is fabricated from a single sheet 32 of pliable material, such as cotton cloth, which is cut along the pattern illustrated in FIG. 5 to provide two identical panels 40 and 41 which are then folded about a fold line 23 to the confronting positions illustrated in FIG. 7 or rolled into a tubular configuration as illustrated in FIGS. 1-4 with the free terminal edge portions, generally designated 34 and 36, disposed in confronting relation and sewn or otherwise coupled together along an upper stitch line 38 to provide an upper border 33 of a predetermined length 33A and a lower border, generally designate 35, of a substantially greater length. The lower border 35 includes a forward lower border portion 37 of a predetermined length 37A which is greater than the upper border length 33A and a rear lower border portion 39 having a predetermined shorter length 39A which is substantially less than the upper border length 33A.

The pliable material for the sheet 32 may suitably comprise cloth fabric which is porous and is of sufficient length to loosely receive the forearm 28 and allow the passage of ambient air thereto. The tubular arm support 22 includes first and second, elongate, substantially identical opposing sidewall panels, generally designated 40 and 41, having upper edges or borders 42 and 44, respectively, and lower edges or borders 43 and 45, respectively.

As illustrated in FIGS. 5 and 7, the lower borders 43 and 45 are integrally coupled together at fold line 23, however, it should be understood that individual panels 40 and 41 could be utilized and stitched or otherwise coupled together. The upper borders 43 and 45 are initially disposed in the same plane (FIG. 5). The lower edges or borders 43 and 45 of panels 40 and 41, respectively, include front lower edge or border portions 46A and 47A, respectively, each having a length 37A and rear lower edge or border portions 46B and 47B, respectively, each of a lesser length 39A. It should be noted that the lower rear edge portions 46B and 47B in the "laid out" planar positions illustrated in FIG. 5 initially diverge rearwardly and are thereafter coupled together to form the lower rear edge portion 39 which is upwardly rearwardly inclined relative to the front lower edge portion 35 to form an elbow receiving pocket 54.

It should be noted that the length 37A of the front lower edge or border portion 35 is substantially longer than the rear pocket forming lower edge or border portion 39. The front lower edge portions 46A and 47A form the front lower edge or border 35 and the rear lower edge or border portions 46B and 47B are stitched together at 53 to form the lower front lower rear edge portion 39 and are of the same length 39A.

The confronting side panels 40 and 41 include confronting front edges 60 and 61, respectively, and confronting rear edges 62 and 63, respectively which, when folded about junction 23 from the flattened or planar condition illustrated in FIG. 5 to the folded position in FIG. 7, or rolled to the rolled, operative tubular position illustrated in FIGS. 1-4, cooperate to form a front opening 64 of a predetermined breadth or diameter 65 and a rear opening 66 having a predetermined larger breadth or diameter 67 through which the user's arm is positioned in the tube 22. In the folded confronting positions of the panels 40 and 41 illustrated in FIGS. 1, 3 and 7. The junction 23 defines the lower front border 37.

The upper border 33 and lower front border 37 rearwardly diverge from the front plane 70 to the beginning point 58 of the upwardly inclined pocket forming border 39 which, as illustrated in FIG. 1, converges upwardly. It should also be noted that the entire upwardly inclined pocket forming rear lower border 39, commencing at 58, is disposed rearwardly of the upper border 33. The junction of the rear end of the upper border 33 and the upper ends of the rear edges 62 and 63 is identified by the reference numeral 89.

It should also be noted that the breadth 59 of the tubular passage portion located at line Z extending between the junction 89 and the opposite point 58 at the front end 58 of the rear pocket forming lower border portion 39 is larger than either of the breadths 65 or 67 of front and rear end openings 64 and 66, respectively.

It is further noted in FIG. 1 that the junction 87 of the rear end of pocket forming rear border portion 39 and the lower ends of the rear edges 62 and 63 is at a higher level than the junction 88 of the front end of the front lower border portion 37 and the lower ends of the front confronting edges 60 and 61.

A pair of longitudinally spaced fastener strips 69 and 71 are fixed to the upper border 34. It is noted that the longitudinal midpoint 74 of the rear strap 71 is positioned substantially along the junction 89 of the rear edges 62 and 63 and upper border 33.

As illustrated in FIG. 1, the front confronting edges 60 and 61, forming the front opening 64, lie in a plane 70 and the rear opening forming confronting edges 62 and 63 lie in a second plane 72 forming the rear opening 66, which upwardly converges toward the plane 70.

The neck strap 24 comprises an elongated carrier line 82 having terminal ends mounting a pair of male fasteners 84 which are detachably received by a pair of complementally formed female fastener receptacles 78 coupled to the pair of short fastener strips 69 and 71 that are sewed or otherwise attached to the upper border portions 34 and 36. A suitable pad or cushion 86 may be placed on the upper strap 82 to provide the user with additional comfort while wearing the sling.

The sling, constructed according to the present invention, includes no obstructing vertical back wall that must be negotiated in order to insert the arm into the tube.

The Operation and Method

A pliable sheet of fabric material 32 is cut to the shape illustrated in FIG. 5 providing substantially identically shaped panels 40 and 41 which are the mirror images of each other joined at a fold line 23. Initially, the pocket forming lower rear border portions 46B and 47B rearwardly diverge relative to each other and the front edges or borders 46A and 47A lie in the same plane. The panels 40 and 41 are folded toward each other about the fold line 23 so that the upper borders 34 and 36 are disposed in confronting relation and stitched together at 38 to provide the upper border 33 as illustrated in FIGS. 1-4. The confronting lower rear terminal ends 46B and 47B are also stitched or otherwise coupled together to form the elbow receiving pocket 54 along the rear lower end portion of the arm receiving tube. The cooperating fasteners 78 and 84 are coupled together and the neck strap 86 is disposed over the user's neck and support thereon.

The user's arm supported by the tube 22 can be disposed across the font of the user's chest and the straps 82 may be adjusted on fasteners 84 until the pocket 54 is disposed at a level not lower than the level of the patient's elbow 30. The patient need not be concerned about positioning the elbow 30 at the exact location but merely slips the arm through the opening end or opening 66 until the forearm 28 is disposed in the tubular section 22 and the elbow 30 is disposed in the elbow receiving pocket 54 as illustrated in FIG. 1. The substantially shorter length 33A of the upper border 33 relative to the length 37A of the lower border 37 and the relative larger diameter rear opening 66 allows the user to easily dispose the arm 28 within the tube passage.

It is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claimed is:

1. An arm sling for supporting the arm of a patient comprising:
   an elongate open ended arm support tube of pliable material having a front end tubular portion which has a breadth that gradually rearwardly increases from a front end opening having a predetermined breadth,
   a rear end tubular portion having a rear end opening having a greater predetermined breadth greater than the front end opening predetermined breadth, and
   an elbow receiving tubular pocket portion, between said front tubular portion and rear end tubular portions and near the rear end tubular portions, having a greater predetermined breadth greater than the rear end tubular portion predetermined breadth; and
   a neck strap support means detachedly coupled at said arm support tube for dependently supporting said tube from the neck of a patient.

2. The arm sling set forth in claim 1 wherein said front end tubular portion and said rear end tubular portion include upwardly converging front and rear terminal edges, respectively, defining said front end opening and said rear end opening, respectively.

3. The arm sling set forth in claim 2 wherein said front terminal edge lies in a first plane and said rear terminal edge lies in a second plane which upwardly converges toward said first plane.

4. The arm sling set forth in claim 3 wherein said front end tubular portion includes an upper terminal border and a front lower terminal border; said upper terminal border and said front, lower terminal border diverging rearwardly relative to each other.

5. The arm sling set forth in claim 4 wherein said elbow receiving tubular pocket portion includes a lower rearward border which extends in a direction upwardly rearwardly away from said front lower border of said front end portion.

6. The arm sling set forth in claim 1 wherein said support tube comprises a single unitary sheet of fabric having a pair of identical patterns disposed in confronting relation and include lower terminal ends coupled together to form a lower terminal border.

7. The arm sling set forth in claim 6 wherein said pliable material comprises a sheet of uniform fabric throughout its length.

8. The arm sling set forth in claim 7 wherein said pliable material is inelastic.

9. The arm sling set forth in claim 6 wherein predetermined breadths are all of such dimensions as to be substantially greater than the breadth of the patient's arm to be supported therein.

10. The arm sling set forth in claim 1 herein said front end portion includes upper and lower, rearwardly diverging borders.

11. The arm sling set forth in claim 1 wherein said open ended arm support tube of pliable fabric material includes
first and second, elongate opposing substantially identical confronting sidewall panels each having
upper and lower borders which confront said upper and lower borders, respectively, of the other panel, and
front and rear terminal edges, spanning said upper and lower borders;
said front and rear terminal edges of each panel confronting said front and rear terminal edges, respectively, of the other panel to form said front end opening between said front confronting edges of said predetermined breadth, respectively, and said rear end opening between said rear confronting edges of said second greater predetermined breadth.

12. The arm sling set forth in claim 11 wherein
each of said lower borders of each panel include front and rear lower border portions coupled in confronting relation with the front and rear lower border portions, respectively, of the other panel;
each of said rear lower border portions having a predetermined length and each of said front lower border portions having a substantially greater predetermined length than said rear lower border portions;
said rear lower border portion of each panel being upwardly inclined relative to the front lower border portion of each panel and having a rear terminal end coupled to a lower end or said rear terminal edge.

13. The arm sling set forth in claim 12 wherein
said upper border of each panel is coupled to the upper border of the other panel and having a upper border predetermined length greater than said predetermined length and less than said rear lower border portion predetermined length;
said upper border and said front lower border portion of each panel diverging in a rearward direction relative to each other.

14. The arm sling set forth in claim 13 wherein
said rear lower border portion is disposed rearwardly of said upper border; said upper border includes a rear end terminating at an upper end of said rear edge of each panel; said front and rear edges upwardly converging.

15. The arm sling set forth in claim 13 wherein said rear lower border portions of said first and second sidewall panels cooperate to form an elbow receiving pocket for receiving the elbow of an arm supported by the support tube.

16. The arm sling set forth in claim 13 wherein said first and second sidewall panels are collectively formed of a single, one-piece panel of pliable fabric material having first and second identical patterns folded into confronting relation.

17. The arm sling set forth in claim 11 wherein said upper border has a predetermined length and said lower border has a substantially greater predetermined length than said upper border; said lower border including front and rear lower border portion disposed in confronting relation with said front and rear lower border portions of the other panel, said rear lower border portion having a predetermined length less than said upper border predetermined length and being upwardly inclined relative to said front lower border portion.

18. The arm sling set forth in claim 17 wherein said front lower border portion has a predetermined length greater than said rear lower border portion predetermined length and greater than said upper border predetermined length.

19. An arm sling comprising:
an open ended, elongate arm support tube of pliable fabric for loosely receiving and supporting a portion of a patient's arm, said sling including
a tubular sidewall, defining
a forward opening of a first predetermined breadth, and a rear opening of a second greater predetermined breadth, greater than said predetermined breadth and an elongate passage therebetween;
said sidewall diverging rearwardly from said forward opening to an elbow receiving pocket portion of a third predetermined breadth, greater than said second predetermined breadth, and thence converging in a rearward direction to said rear opening; and
neck strap means for dependently supporting the arm support tube on the neck of the patient.

20. The arm sling set forth in claim 19 wherein said fabric is inelastic.

21. The arm sling set forth in claim 19 wherein said tubular sidewall includes an upper border having a predetermined length and a lower border having a substantially greater predetermined length greater than said upper border predetermined length.

22. The arm sling set forth in claim 21 wherein said lower border includes front and rear lower border portions; said rear lower border portion having a predetermined length less than said upper border predetermined length and being upwardly rearwardly inclined relative to said front lower border portion; said front lower border portion having a predetermined length substantially greater than said upper border predetermined length.

23. The arm sling set forth in claim 22 wherein said tubular sidewall includes front and rear edges, spanning opposite ends of said upper and lower borders, forming said forward and rear openings, respectively.

24. The arm sling set forth in claim 23 wherein said front and rear edges upwardly converge.

25. An arm sling comprising:
an open ended, elongate, arm support tube of pliable fabric for detachably, loosely receiving a portion of a user's arm, said sling including a sidewall defining an elongate passage having a forward terminal end opening of a first predetermined breadth and diverging in a rearward direction from said forward terminal end to an elbow opening receiving pocket portion of a second greater predetermined breadth and thence converging in a rearward direction to a rear terminal end opening of a third predetermined breadth greater than said first predetermined breadth and less than said second predetermined breadth; and neck strap means for dependently supporting the arm support tube form the neck of a user.

26. The arm sling set forth in claim 25 wherein said arm support tube comprises a one piece sheet of material having first and second identical side wall portions disposed in confronting relation and including front and rear terminal edges coupled together to form said forward and rear end openings, respectively.

27. The arm sling set forth in claim 25 wherein said arm support tube comprises a single sheet of cloth, having terminal ends fixed to each other defining said passage.

28. An arm sling comprising:

an open ended, elongate arm support tube including
a single sheet of pliable fabric folded over on itself to provide
a forward end opening of a predetermined breadth and a rear end opening of a greater predetermined breadth;
a lower border including
a generally linear, forwardly disposed, lower border wall portion extending rearwardly from said forward end opening and
a rearwardly disposed lower border wall portion upwardly rearwardly inclined relative to said forwardly disposed border wall portion and terminating at said rear end opening;
said single sheet further including upper terminal ends coupled together to form a forwardly disposed upper wall portion diverging in a rearward direction, relative to said forwardly disposed lower wall portion and converging in a rearward direction relative to said upwardly inclined rearwardly disposed lower wall border portion.

29. An arm sling comprising an open ended, elongate arm support sleeve having
a front opening, of a predetermined breadth, having upper and lower ends; and
a rear opening, of a greater predetermined breadth, having upper and lower end;
said support tube comprising a pliable fabric sheet, folded upon itself and having front and rear terminal ends, coupled together to define an elongate passage between said front and rear openings and including
an upper, generally linear closed upper wall portion longitudinally extending between said upper ends of said forward and rear openings and
a lower closed wall portion extending between said lower ends of said forward and rear openings,
said lower, closed wall portion including
a forward, generally linear, lower wall portion rearwardly diverging away from said upper linear wall portion and
a rearward upwardly rearwardly inclined rear lower wall portion which is upwardly inclined in a rearward direction relative to said forward lower wall portion.

30. An arm sling for supporting an arm in a generally horizontal position comprising an open ended support sleeve of pliable fabric material including
first and second, elongate opposing substantially identical confronting sidewall panels each having
upper and lower borders which confront said upper and lower borders, respectively, of the other panel, and
front and rear edges, spanning said upper and lower borders and confronting said front and rear edges, respectively, of the other panel;
each of said lower borders of each panel including front and rear lower border portions coupled in confronting relation to the front and rear lower border portions, respectively, of the other panel;
each of said rear lower border portions having a first predetermined length and each of said front lower border portions having a second substantially greater predetermined length;
said rear lower border portion of each panel being upwardly inclined relative to the front lower border portion of each panel and having a rear terminal end coupled to a lower end said rear edge;
said upper border of each panel being coupled to the upper border of the other panel and having a third predetermined length greater than said first predetermined length and less than said second predetermined length;
said upper border and said front lower border portion of each panel diverging in a rearward direction relative to each other;
said front edge of each panel confronting said front edge of the other panel to form a front opening of a predetermined breadth; said rear edge of each panel confronting said rear edge of the other panel to form said rear opening of a greater predetermined breadth; and
neck strap means coupled to at least one of said upper borders for dependently supporting said support sleeve.

31. The arm sling set forth in claim 30 wherein said rear lower border portion is disposed rearwardly of said upper border of each panel.

32. The arm sling set forth in claim 30 wherein said upper border includes a rear end terminating at an upper end of said rear edge of each panel.

33. The arm sling set forth in claim 30 wherein said front and rear edges lie in first and second upwardly converging planes, respectively.

34. The arm sling set forth in claim 30 wherein said rear lower border portions of said first and second sidewall panels cooperate to form an elbow receiving pocket for receiving the elbow of an arm supported by the sleeve.

35. The arm sling set forth in claim 30 wherein said rear lower border portions are upwardly inclined in a direction toward said front lower border portions.

36. The arm sling set forth in claim 30 wherein said front lower border portions of said first and second sidewall panels are unitary.

37. The arm sling set forth in claim 30 wherein said first and second sidewall panels are formed of a single, one-piece panel of pliable fabric material having first and second identical patterns folded into confronting relation.

38. The arm sling set forth in claim 30 wherein the junction of said rear terminal end of rear lower border portion and the lower end of said rear edge is at a level above the junction of said lower ends of said front edges and said lower front border portion.

* * * * *